US005505192A

United States Patent [19]
Samiotes et al.

[11] Patent Number: 5,505,192
[45] Date of Patent: Apr. 9, 1996

[54] DISPENSER MONITORING SYSTEM

[75] Inventors: Nicholas G. Samiotes, Westwood; James G. Bath, Concord, both of Mass.

[73] Assignee: New-Med Corporation, Waltham, Mass.

[21] Appl. No.: 280,068

[22] Filed: Jul. 25, 1994

Related U.S. Application Data

[63] Continuation-in-part of Ser. No. 151,112, Nov. 12, 1993, abandoned.

[51] Int. Cl.$^6$ ................................................. A61M 11/00
[52] U.S. Cl. ................................. 128/200.14; 128/200.23
[58] Field of Search ......................... 128/200.14, 200.23; 222/30, 36, 37, 38

[56] References Cited

U.S. PATENT DOCUMENTS

| | | | |
|---|---|---|---|
| 3,119,557 | 1/1964 | Chapman | 222/36 |
| 3,170,597 | 2/1965 | Reichenberger | 222/30 |
| 3,831,812 | 8/1974 | Dolan | 222/36 |
| 3,845,883 | 11/1974 | Johnson et al. | 222/30 |
| 4,034,757 | 7/1977 | Glover | 222/30 |
| 4,436,223 | 3/1984 | Wilson | 222/36 |
| 4,538,744 | 9/1985 | Weissenborn | 222/36 |
| 4,736,871 | 4/1988 | Luciani et al. | 222/30 |
| 4,817,822 | 4/1989 | Rand et al. | 222/38 |
| 5,038,972 | 8/1991 | Muderlak et al. | 222/36 |
| 5,284,133 | 2/1994 | Burns et al. | 128/200.23 |
| 5,300,042 | 4/1994 | Kossoff et al. | 222/38 |
| 5,328,597 | 7/1994 | Boldt et al. | 222/36 |
| 5,331,953 | 7/1994 | Andersson et al. | 128/200.23 |
| 5,363,842 | 11/1994 | Mishelevich et al. | 128/200.23 |
| 5,370,267 | 12/1994 | Schroeder | 222/37 |

FOREIGN PATENT DOCUMENTS

| | | | |
|---|---|---|---|
| 0028929 | 5/1981 | European Pat. Off. | |
| 1317315 | 5/1973 | United Kingdom | |
| 8602275 | 4/1986 | WIPO | 128/200.23 |
| 9207600 | 5/1992 | WIPO | 128/200.23 |

*Primary Examiner*—Aaron J. Lewis
*Attorney, Agent, or Firm*—Iandiorio & Teska

[57] ABSTRACT

A dispenser monitoring system for a dispenser actuatable along its actuation axis to dispense a quantity of material includes a housing having a lower portion for mounting on a dispenser and an upper portion having a cavity; and a dispenser monitoring circuit disposed in the cavity including a switching device responsive to actuation of the dispenser container; a counter circuit, responsive to the switching device, for registering that a quantity of material has been dispensed; and a display device, responsive to the counter circuit, for indicating the status of the material in the dispenser.

52 Claims, 5 Drawing Sheets

DISPENSER MONITORING SYSTEM

RELATED CASE

This application is a continuation-in-part of U.S. patent application Ser. No. 08/151,112, filed Nov. 12, 1993, now abandoned, entitled "Improved Function Display Device", by Samiotes et al., which is fully incorporated by reference herein.

FIELD OF INVENTION

This invention relates to a dispenser monitoring system for a dispenser actuatable along its actuation axis to dispense a quantity of material. In one particular application the invention is embodied in an inhalator dosage monitoring system for a metered dose inhalator canister such as used by asthma sufferers.

BACKGROUND OF INVENTION

In many instances proper medical treatment requires accurate doses of medicine to be administered at clearly defined intervals. In such cases it is important that the patient keep an accurate record of his ministrations to be sure that he is abiding by instructions and to permit the attending physician to evaluate the efficiency of the treatment with full confidence in the dosage and timeliness of the ministrations. This is not always easy: people who need medicinal treatment are ill and typically not well disposed to keeping accurate records. Often they are aged or children, which makes accurate record keeping even less likely. One area of concern is the treatment of asthmatics using metered dose inhalator canisters. The canister is installed in an applicator which receives the canister in inverted orientation. The bottom of the canister is facing upward. Actuation is effected by pressing down on the bottom of the canister, which causes the nozzle to be tripped by the structure of the applicator to release a metered dose of medicine. The structure of the applicator redirects the mist 90° horizontally through a tube held between the patient's lips as the patient breathes in.

The metered dose inhaler canister is typically a metal container, and so it is not possible to tell accurately how much medicine or metered dosages are remaining. The patient is at risk to run out at an inopportune time, thus putting himself in jeopardy in many ways, including shortness of breath, choking, respiratory discomfort, and even hospitalization. The metered dose inhalers do not provide the user with daily dosing information. The patient, unless he or she records the information in a diary, has no real chance to remember what has been taken on any given day. The metered dose inhalers do not provide any historical information to the patient or the attending doctor. Unless the patient is very diligent in recording his daily dosing, there is no way he can keep an accurate record for any length of time. Patients tend to be very lackadaisical when recording or managing their medicine. Doctors cannot treat the asthmatic effectively if the information being communicated is poor quality or nonexistent. Because patients are concerned that they may run out of medicine, or do not know how much is remaining in the canister, they will tend to purchase an "extra" unit, an unnecessary expense. Patients are concerned that the medicine contained within the canisters can be harmful if not administered in a controlled manner. Steroids are commonly used in asthma medicines. Parents of young asthmatics in particular are concerned about the intake level of steroidal compounds.

The need for dosage monitoring is not limited to aerosol, atomized, gas or liquid form; it is needed as well for dispensing of solids such as powders and tablets and for candies, cough medicines, breath mints, stomach acid neutralizers and the like.

SUMMARY OF INVENTION

It is therefore an object of this invention to provide an improved dispenser monitoring system.

It is a further object of this invention to provide such an improved dispenser monitoring system particularly useful for inhalator dosage monitoring of metered dose canisters.

It is a further object of this invention to provide such an improved dispenser monitoring system which is operationally transparent to the user in that it monitors each dose automatically upon actuation of the dispenser without any additional action on the part of the user.

It is a further object of this invention to provide such an improved dispenser monitoring system which records the dosage administration over one or more defined time intervals and displays them on request.

It is a further object of this invention to provide such an improved dispenser monitoring system which is small, inexpensive, rugged, and has virtually no moving parts.

It is a further object of this invention to provide such an improved dispenser monitoring system which requires no special training or knowledge to use.

It is a further object of this invention to provide such an improved dispenser monitoring system which is simple to install, attaches securely, is easily removed and transferable to replacement canisters, fits all dispensers, and is compatible with all applications.

The invention results from the realization that a truly effective dispenser monitoring system can be achieved with a housing having a lower portion for mounting a dispenser and an upper portion having a cavity which houses a dispenser monitoring circuit that has a switching device directly responsive to actuation of the dispenser to cause a counter circuit to register that a quantity of material has been dispensed and display the status of the material in the dispenser, e.g., the number of units or doses remaining or already dispensed.

This invention features a dispenser monitoring system for a dispenser actuatable along its actuation axis to dispense a quantity of material. There is a housing having a lower portion for mounting on a dispenser and an upper portion having a cavity. There is a dispenser monitoring circuit disposed in the cavity and including a switching device response to actuation of the dispenser, a counter circuit responsive to the switching device for registering that a quantity of material has been dispensed, and a display device responsive to the counter circuit for indicating the status of the material remaining in the dispenser.

In a preferred embodiment the lower portion of the housing may be flexible for securely gripping the dispenser. The dispenser may be disposed in an applicator and the lower portion of the housing may have a thin wall for gripping the dispenser without interfering with the applicator. The lower portion may be tubular and it may be tapered to be narrow at the lower end for accommodating a range of sizes of dispensers. The upper and lower portions may be separate but connected, or they may be integral. The upper portion may include an upper member having a window for viewing the display device. The lower member may be rigid for providing a reference stop for the switching device. The switching device may be aligned with the actuator axis of the dispenser for responding to the actuator force applied to the dispenser to sense the dispensing of a quantity of material. The counter circuit may count the number of quantities of material dispensed. The display device may display the number of quantities of material remaining in the dispenser to be dispensed. The force required to actuate the switching device may be less than that required to actuate the dispenser. The dispenser monitoring circuit may include means for loading into the counter circuit the number of quantities of material contained in the dispenser. The display device may include a storage device for accumulating and storing for display the history of the number of dispenser actuations in a predetermined time period. The predetermined time period may be twenty-four hours or it may be thirty days, or both. The storage device may accumulate and store for display the daily history of dispenser actuation for thirty days. The upper member may be momentarily deflectable by the actuation force applied to actuate the dispenser to move the dispenser monitoring circuit in the cavity to operate the switching device. The dispenser monitoring circuit may include an indicator device for indicating that an actuation has occurred. The indicator device may produce an audible tone to indicate that an actuation has occurred. The dispenser monitoring device may include an alarm circuit for indicating when less than a predetermined number of quantities of material remain to be dispensed. The alarm circuit may produce at least one of an audible and visual indication. The dispenser monitoring circuit may include a reset circuit for clearing the present display of the count of the quantities of material remaining when the dispenser being monitored is replaced. The upper portion of the housing may include a raised ridge which extends beyond the upper member for preventing false actuation of the switching device.

The invention also features an inhalator dosage monitoring system for a metered dose inhalator canister actuatable along its actuation axis to dispense a metered dose. There is a housing having a lower portion for mounting on a metered dose inhalator canister and an upper portion having a cavity, and a dosage monitoring circuit disposed in the cavity and including a switching device responsive to actuation of the canister, a counter circuit responsive to the switching device for registering that a dose has been dispensed, and a display device responsive to the counter circuit for indicating the number of doses remaining in the canister.

In a preferred embodiment the lower portion of the housing may be flexible for securely gripping the inhalator canister. The inhalator canister may be disposed in an applicator and a lower portion of the housing may have a thin wall for gripping the inhalator canister without interfering with the applicator. The lower portion may be tubular and it may be tapered to be narrower at the lower end for accommodating a range of sizes of the inhalator canister. The upper and lower portions may be separate but connected or they may be integral. The upper portion may include an upper member having a window for viewing the display device. The upper portion may include a lower member which is rigid for providing a reference stop for the switching device. The switching device may be aligned with the actuator axis of the inhalator canister for responding to the actuator force applied to the inhalator canister for responding to the actuating force applied to the inhalator canister to sense the dispensing of the dose. The counter circuit may count the number of doses dispensed. The display device may indicate the number of doses in the inhalator canister to be dispensed. The force required to actuate the switching device is less than or equal to that required to actuate the inhalator device. The dosage monitoring circuit may include means for loading into the counter circuit the number of doses contained in the inhalator canister. The display device may include a storage device for accumulating and storing for display the history of the number of inhalator canister actuation in a predetermined time period. The predetermined time period may be twenty-four hours, thirty days, or both. The storage device may accumulate and store for display the daily history of inhalator canister actuation for thirty days. The upper member may be momentarily deflectable by the actuation force applied to actuate the inhalator canister to move the dosage monitoring circuit in the cavity to operate the switching device. The dosage monitoring circuit includes an indicator device for indicating that actuation has occurred. The indicator device may produce an audible tone to indicate that actuation has occurred. The dosage monitoring device may include an alarm circuit for indicating when less than a predetermined number of doses remain to be dispensed. The alarm circuit may produce at least one of an audible and visual indication. The dosage monitoring circuit may include a reset circuit for clearing the present display of the count of doses remaining when the inhalator canister being monitored is replaced. The upper portion may include a raised ridge which extends beyond the upper member for preventing false actuation of the switching device.

DISCLOSURE OF PREFERRED EMBODIMENT

Other objects, features and advantages will occur to those skilled in the art from the following description of a preferred embodiment and the accompanying drawings, in which.

Figure 2:
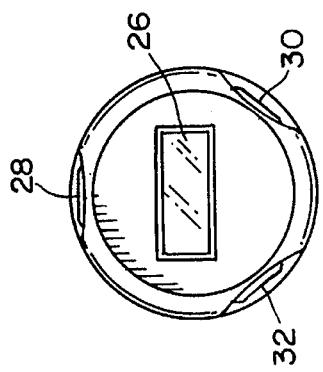
FIG. 2 is a top plan view of the dispenser monitoring system of FIG. 1.
Figure 1:
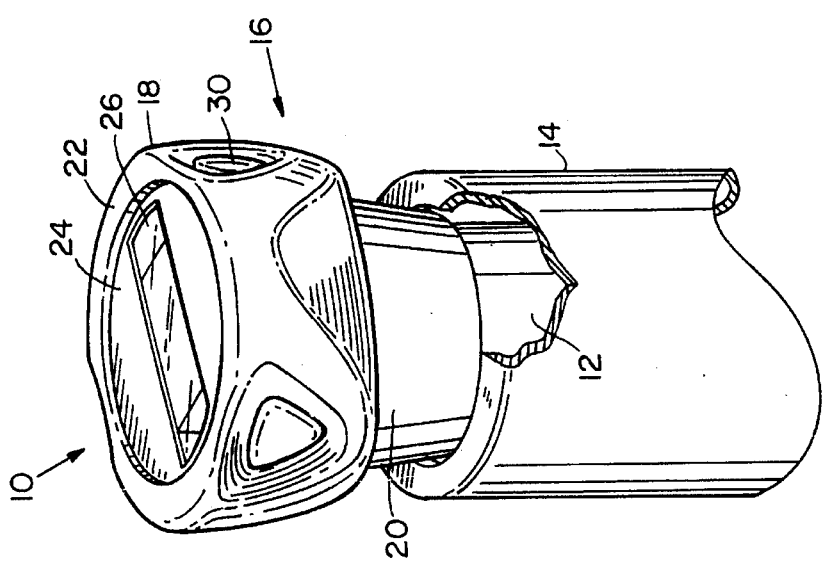
FIG. 1 is a perspective view of a dispenser monitoring system according to this invention mounted on a canister installed in an applicator, only a portion of which is shown.

There is shown in FIG. 1 a dispenser monitoring system in the nature of an inhalator dosage monitoring system 10 installed on a metered dose inhalator canister 12 mounted in applicator 14. The inhalator dosage monitoring system 10 includes a housing 16 which has an upper portion 18 and lower portion 20. Upper portion 18 has a ridge 22 recessed below which is upper member 24 which contains a window 26, more readily visible in FIG. 2, through which the number of doses remaining or number of doses dispensed, as well as the history of the past twenty-four hours, or thirty days, or forty-eight hours, or week, or month, can be displayed. There are three finger-operated side switches indented to prevent false activation: set switch or key 28, which enables the user to set in the number of total doses contained in the canister; history switch 30, which enables the user to recall the history of medication over the past twenty-four hours, forty-eight hours, thirty days, or any other interval; and clear switch 32, which enables the user to clear the present count so that a depleted canister can be replaced with a new one while still preserving the twenty-four or thirty day or other interval count.

Figure 3:
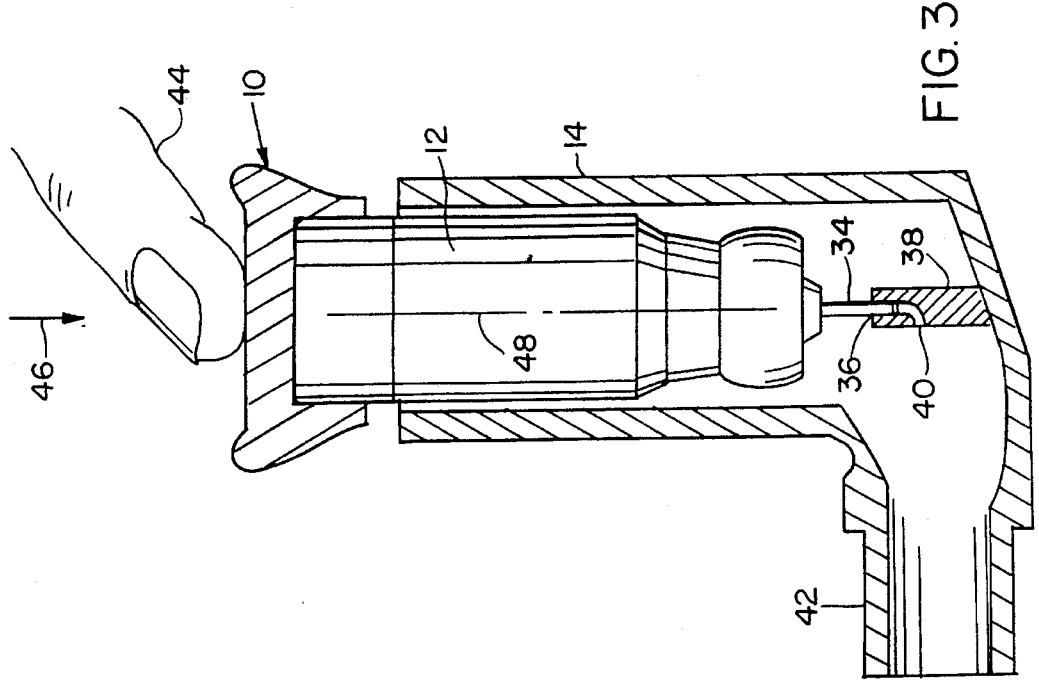
FIG. 3 is a side sectional elevational view showing the installation of a metered dose inhalator canister in an applicator with the dispenser monitoring system of this invention in place.

The operation of canister 12 in applicator 14 can be better seen in FIG. 3, where the canister has been installed upside down so that its aerosol nozzle 34 is gripped in hole 36 of stud 38 which contains channel 40 that has a right angle bend. Applicator 14 also has an enlarged nozzle 42 which is to be placed between the lips of the user. In use, the user presses a finger 44 downwardly in the direction of arrow 46, thereby applying an actuation force along actuation axis 48 of canister 12. This moves canister 12 down against its stationarily held nozzle 34, causing the aerosol driven medicine to dispense through channel 40 and out nozzle 42 into the mouth and lungs of the user. The same action of finger 44 which causes canister 12 to dispense its medication also operates a switch in inhalator dosage monitoring system 10 to record the dispensing of a dose of medication.

Figure 4:
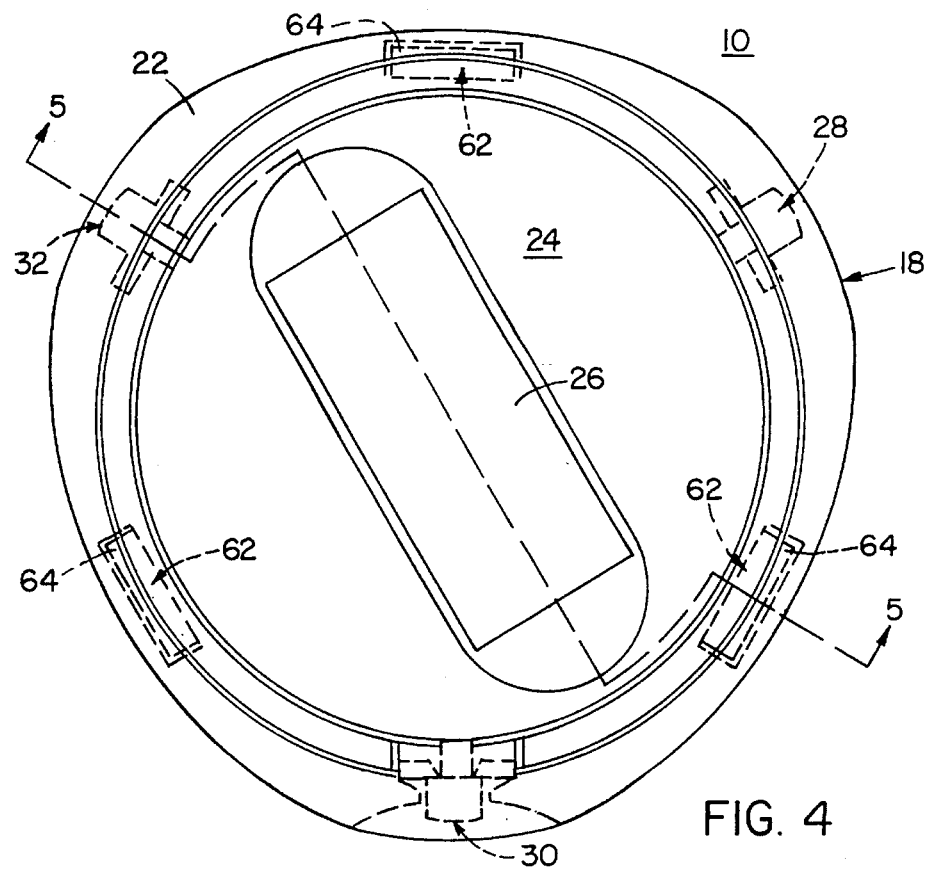
FIG. 4 is an enlarged more detailed top plan view similar to that of FIG. 2.
Figure 5:
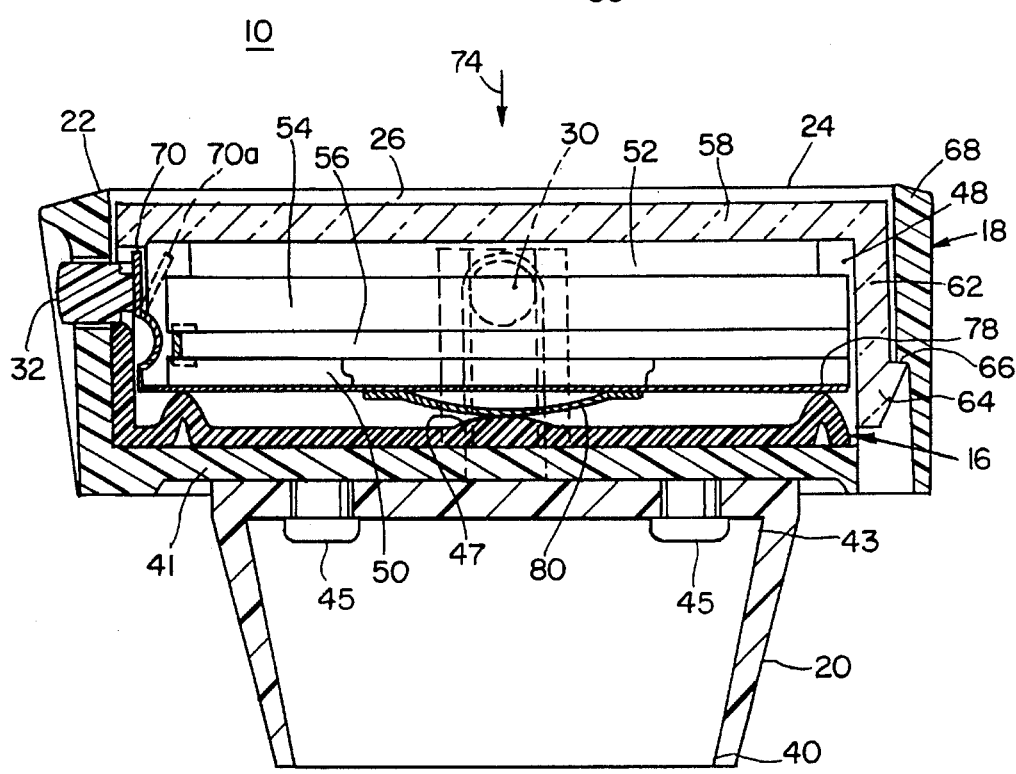
FIG. 5 is a sectional view taken along line 5—5 of FIG. 4.

Housing 16, FIGS. 4 and 5, shows the canister container lower portion 20 is tapered inward slightly so that it is smaller at its lower end 40 than at its upper end 43. This is done so that a wide range of canister diameters can be accommodated. Lower portion 20 is made from a flexible, typically elastomeric material for the same purpose. Upper portion 18 is typically more rigid. Lower portion 20 is attached to upper portion 18 by means of rivets, adhesives or screws 45. Lower member 41 of upper portion 18 is made fairly rigid to act as a stop for the elastomeric gasket switch or membrane switch 47 which is disposed in the bottom of cavity 48 provided in upper portion 18. Cavity 48 also has space for battery 50, display 52, the electronic module 54, and supporting PC board 56. A plastic lens 58 extends over the top of display 52 and culminates in downwardly extending shoulders 62 which end in snap tabs 64 that engage overhangs 66 on outer sleeve 68 of upper portion 18. Each switch or button 28, 30 and 32 protrudes slightly as shown at side contact button 32, FIG. 5, so it can be pushed slightly inwardly and move contact 70 inwardly slightly to the place indicated at 70a to close the contact to provide a signal to electronic module 54, which in the case of button 32 produces a clear signal. When inhalator dosage monitoring system 10 is installed on a canister a downward force in the direction of arrow 74, FIG. 5, moves the entire monitoring system including display 52, electronic module 54, board 56, battery 50, and lens 58, downwardly slightly, as much as 0.040 inch, to cause metal contact plate 78 and its switch actuator 80 to press on and actuate membrane switch 46. This is done inadvertently, unknowingly by the user when the user acts in a normal fashion to operate the canister to administer a dose of medicine to himself. No other action is required to monitor the dosage, record it, and store it for future reference.

Figure 6:
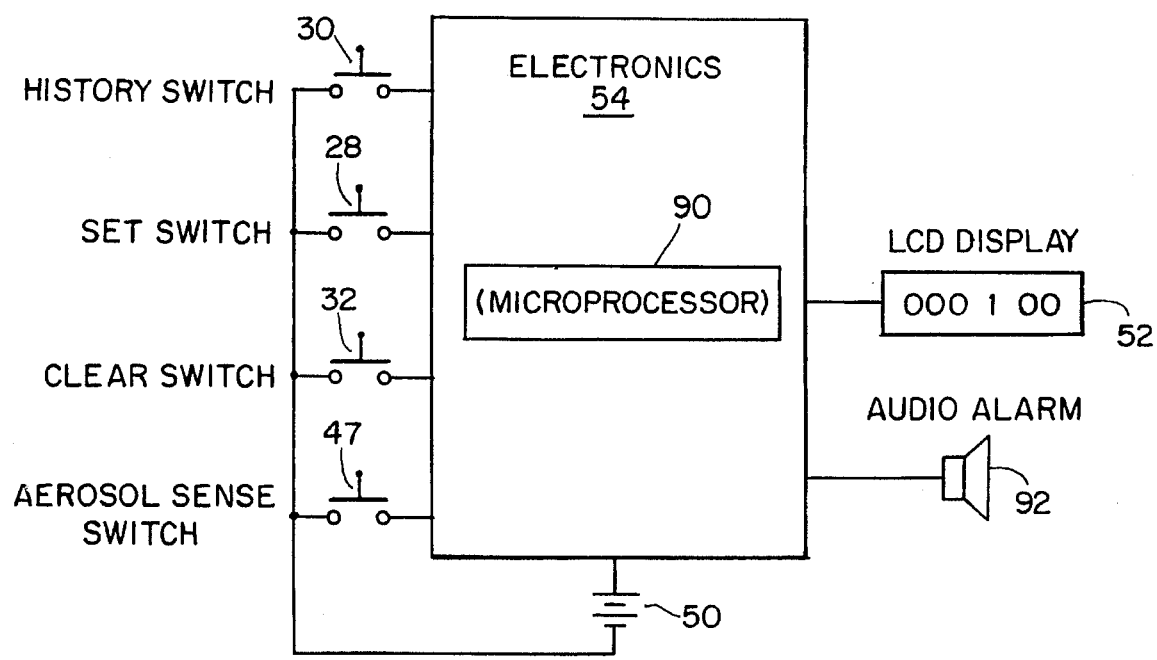
FIG. 6 is a functional block diagram of the dispenser monitoring circuit according to this invention.
Figure 7:
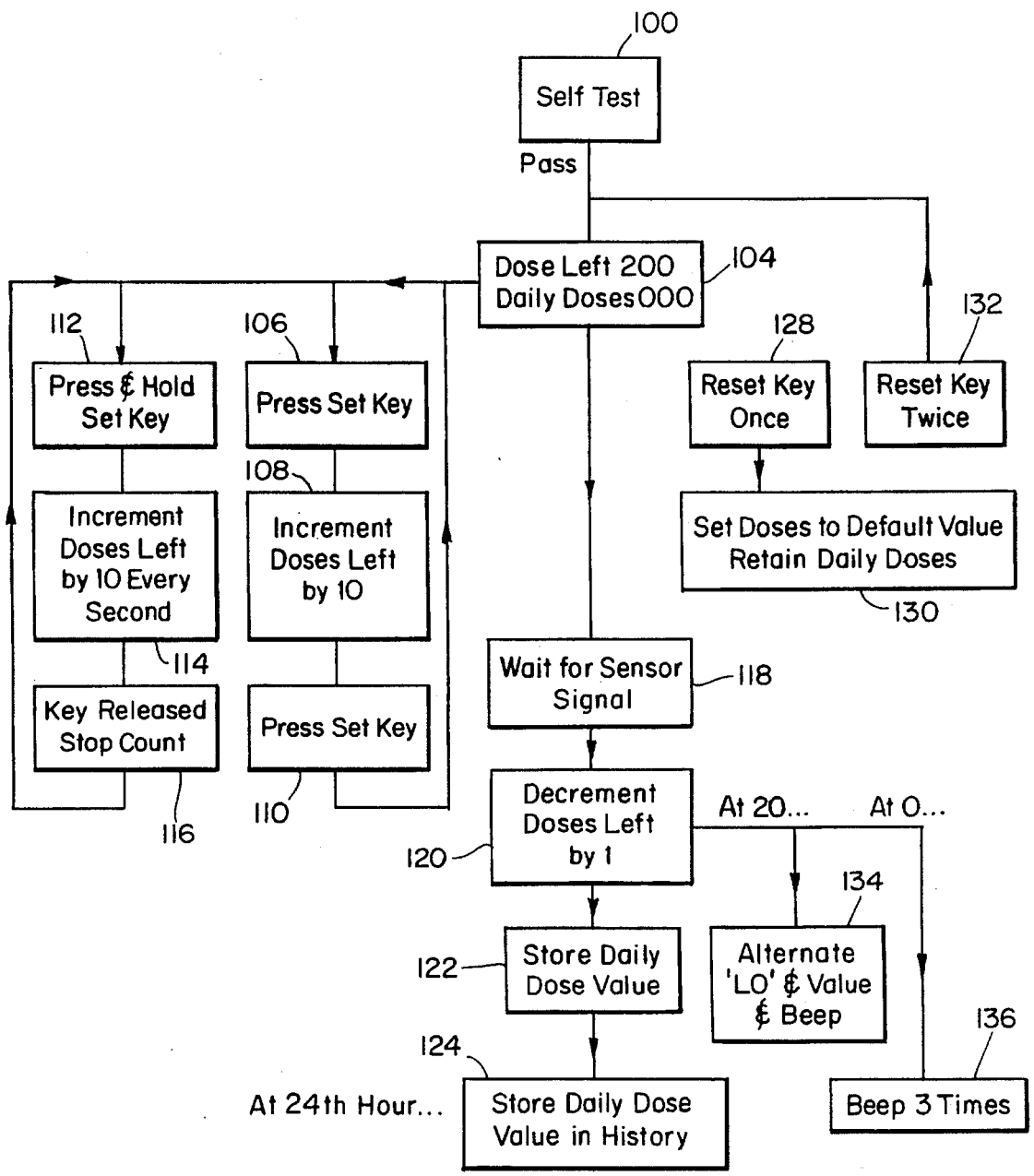
FIG. 7 is a flow chart showing the software program which operates the microprocessor of FIG. 6.

Electronic module 54, FIG. 6, typically includes a microprocessor such as a SMOS four-bit microprocessor operated by a 1.5/3.0 volt battery 90. An audio alarm 92 is supplied to indicate when a dose has been delivered, when fewer than a predetermined number of doses are remaining and/or when there are no doses remaining, as will be explained with reference to FIG. 7. Microprocessor 90 is programmed to operate as shown by the flow chart in FIG. 7. Subsequently the indicator displays, step 104, that the doses remaining are 200 and that today's (daily) doses so far are zero. In order to increment the number of doses remaining, for example when a new canister replaces an old one, the set key is pressed, step 106, to increment the doses remaining by ten, step 108. If further incrementing is needed the set key is pressed again in step 110. If a large number of increments are required, the set key may be pressed and held, step 112, so that the number of doses are incremented by ten every second, step 114, until the key is released in step 116. When a sensor signal occurs in step 118, the doses remaining are decremented by one in step 120 and the daily dose value is stored in step 122. At the twenty-fourth hour the daily dose is stored in "history" as per step 124 for the last twenty-four hours. The clear key is hit once, step 128, to set the doses to a default value of 000 but retains the daily dosage value as shown in step 130. To exit, the clear key is hit twice (within five seconds) in step 132. When the number of doses remaining goes as low as twenty, the display alternately displays the number remaining and beeps three times as indicated in step 134. When there are no doses remaining, the system beeps three times as indicated in step 136.

Figure 8:
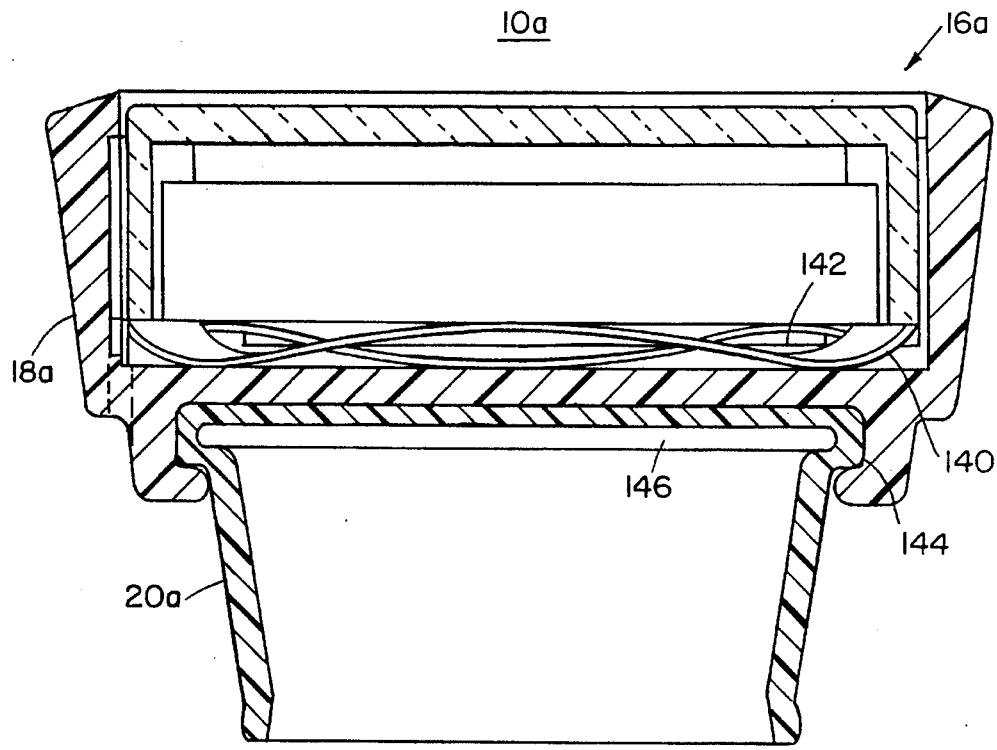
FIG. 8 is a side elevational sectional view of an alternative construction of the dispenser monitoring system of this invention.

In an alternative construction, monitoring system 10a, FIG. 8, may use a wave spring 140 and a travel limiter 142 to control the switching operation. In addition, as shown in FIG. 8, the lower portion 20 may be snap-fitted into recess 144 and upper portion 18a and then held securely in place by a rigid retainer ring or plate 146.

Figure 9:
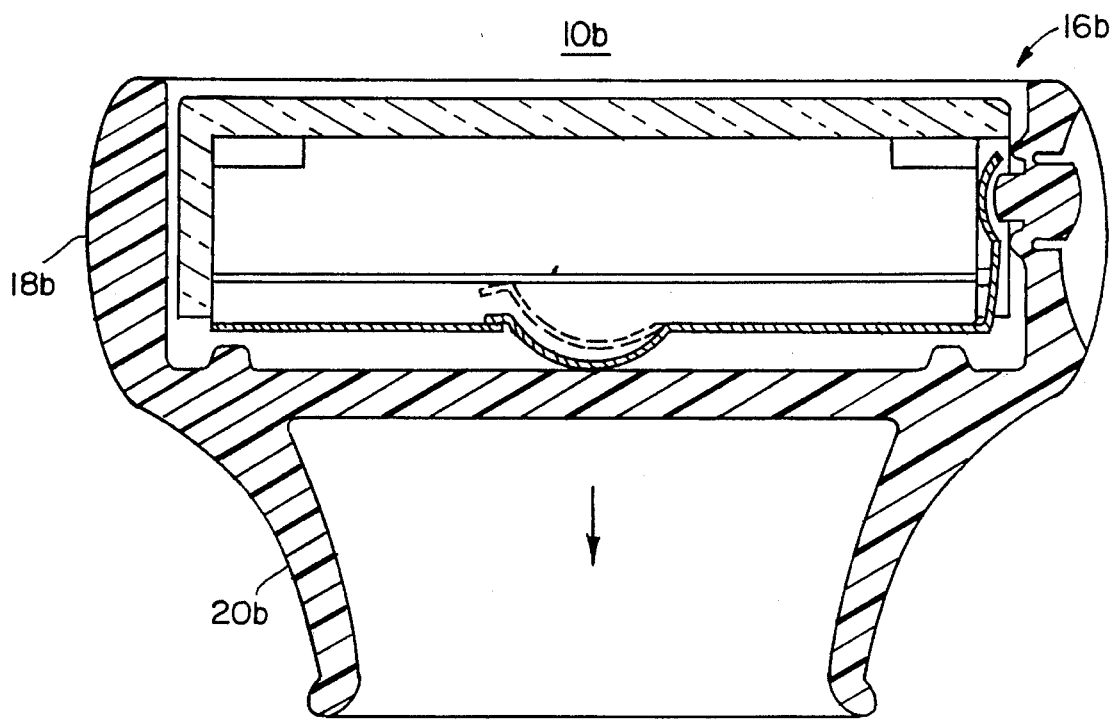
FIG. 9 is a side elevational sectional view of another alternative embodiment of the dispenser monitoring system of which invention.

Alternatively, housing 16b of monitoring system 10b, FIG. 9, may be made so that the upper portion 18b and lower portion 20b are integrally formed.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An electronic dispenser monitoring system for a dispenser actuatable along an actuation axis to dispense a quantity of material, comprising:

a housing having a lower portion for mounting on a dispenser and an upper portion having a cavity; said actuation axis extending from said upper portion through such a dispenser which is affixed to the lower portion of said housing; and an electronic dispenser monitoring circuit disposed in said cavity and including a switching device including an elastomeric membrane switch and at least one contact plate which is engaged by said membrane switch in response to actuation of such a dispenser, a counter circuit, responsive to said switching device, for registering that a quantity of material has been dispensed, and a display device, responsive to said counter circuit, for indicating the status of the material in such a dispenser;

said upper portion further including a rigid lower member which acts as a stop for said elastomeric membrane switch, said elastomeric membrane switch actuating said switching device via said at least one contact plate in response to actuation of such a dispenser.

2. The dispenser monitoring system of claim 1 in which said lower portion of said housing is flexible for securely gripping the dispenser.

3. The dispenser monitoring system of claim 1 in which the dispenser is disposed in an applicator and said lower portion of said housing has a thin wall for gripping said dispenser without interfering with the applicator.

4. The dispenser monitoring system of claim 1 in which said lower portion is tubular.

5. The dispenser monitoring system of claim 4 in which said lower portion is tapered to be narrower at the lower end for accommodating a range of sizes of dispensers.

6. The dispenser monitoring system of claim 1 in which said upper and lower portions are separate but connected.

7. The dispenser monitoring system of claim 1 in which said upper and lower portions are integral.

8. The dispenser monitoring system of claim 1 in which said upper portion includes an upper member having a window for viewing said display device.

9. The dispenser monitoring system of claim 8 in which said switching device is aligned with the actuation axis of the dispenser for responding to the actuation force applied to the dispenser to sense the dispensing of a quantity of material.

10. The dispenser monitoring system of claim 9 in which the force required to actuate said switching device is less than that required to actuate the dispenser.

11. The dispenser monitoring system of claim 9 in which said upper member is momentarily deflectable by the actuation force applied to actuate the dispenser to move said dispenser monitoring circuit in said cavity to operate said switching device.

12. The dispenser monitoring system of claim 1 in which said counter circuit counts the number of quantities of material dispensed.

13. The dispenser monitoring system of claim 1 in which said display device displays the number of quantities of material remaining in the dispenser to be dispensed.

14. The dispenser monitoring system of claim 1 in which said dispenser monitoring circuit includes means for loading into said counter circuit, the number of quantities of material contained in the dispenser.

15. The dispenser monitoring system of claim 1 in which said display device includes a storage device for accumulating and storing for display the history of the number of dispenser actuations in a predetermined time period.

16. The dispenser monitoring system of claim 1 in which said predetermined time period is twenty-four hours.

17. The dispenser monitoring system of claim 1 in which said predetermined time period is thirty days.

18. The dispenser monitoring system of claim 17 in which said storage device accumulates and stores for display the daily history of dispenser actuation for thirty days.

19. The dispenser monitoring system of claim 1 in which said dispenser monitoring circuit includes an indicator device for indicating that an actuation has occurred.

20. The dispenser monitoring system of claim 19 in which the indication that an actuation has occurred is an audible tone.

21. The dispenser monitoring system of claim 1 in which said dispenser monitoring device includes an alarm circuit for indicating when less than a predetermined number of quantities of material remain to be dispensed.

22. The dispenser monitoring system of claim 21 in which said alarm circuit produces at least one of an audible and visual indication.

23. The dispenser monitoring system of claim 1 in which said dispenser monitoring circuit includes a reset circuit for clearing the present display of the circuit of the quantities of material remaining when the dispenser being monitored is replaced.

24. An electronic inhalator dosage monitoring system for a metered dose inhalator canister actuatable along an actuation axis to dispense a metered dose comprising:

a housing having a lower portion for mounting on a metered dose inhalator canister, and an upper portion having a cavity; said actuation axis extending from said upper portion through such an inhalator canister which is affixed to the lower portion of said housing; and an electronic dosage monitoring circuit disposed in said cavity and including a switching device including an elastomeric membrane switch and at least one contact plate which is engaged by said membrane switch in response to actuation of such an inhalator canister, a counter circuit, responsive to said switching device, for registering that a dose has been dispensed, and a display device, responsive to said counter circuit, for indicating the number of doses remaining in such an inhalator canister;

said upper portion further including a rigid lower member which acts as a stop for said elastomeric membrane switch, said elastomeric membrane switch actuating said switching device via said at least one contact plate in response to actuation of such an inhalator canister.

25. The dosage monitoring system of claim 24 in which said lower portion of said housing is flexible for securely gripping the inhalator canister.

26. The dosage monitoring system of claim 25 in which said display device displays the number of doses remaining in the inhalator canister to be dispensed.

27. The dosage monitoring system of claim 24 in which the inhalator canister is disposed in an applicator and said lower portion of said housing has a thin wall for gripping said inhalator canister without interfering with the applicator.

28. The dosage monitoring system of claim 24 in which said lower portion is tubular.

29. The dosage monitoring system of claim 28 in which said lower portion is tapered to be narrower at the lower end for accommodating a range of sizes of inhalator canisters.

30. The dosage monitoring system of claim 24 in which said upper and lower portions are separate but connected.

31. The dosage monitoring system of claim 24 in which said upper and lower portions are integral.

32. The dosage monitoring system of claim 24 in which said upper portion includes an upper member having a window for viewing said display device.

33. The dosage monitoring system of claim 24 in which said switching device is aligned with the actuation axis of the inhalator canister for responding to the actuation force applied to the inhalator canister to sense the dispensing of a dose.

34. The dosage monitoring system of claim 33 in which the force required to actuate said switching device is less than that required to actuate the inhalator canister.

35. The dosage monitoring system of claim 33 in which said upper member is momentarily deflectable by the actuation force applied to actuate the inhalator canister to move said dosage monitoring circuit in said cavity to operate said switching device.

36. The dosage monitoring system of claim 24 in which said counter circuit counts the number of doses dispensed.

37. The dosage monitoring system of claim 24 in which said dosage monitoring circuit includes means for loading into said counter circuit, the number of doses contained in the inhalator canister.

38. The dosage monitoring system of claim 24 in which said display device includes a storage device for accumulating and storing for display the history of the number of inhalator canister actuations in a predetermined time period.

39. The dosage monitoring system of claim 38 in which said predetermined time period is twenty-four hours.

40. The dosage monitoring system of claim 24 in which said predetermined time period is thirty days.

41. The dosage monitoring system of claim 40 in which said storage device accumulates and stores for display the daily history of inhalator canister actuation for thirty days.

42. The dosage monitoring system of claim 24 in which said dosage monitoring circuit includes an indicator device for indicating that an actuation has occurred.

43. The dosage monitoring system of claim 42 in which said indicator device produces an audible tone to indicate that an actuation has occurred.

44. The dosage monitoring system of claim 24 in which said dosage monitoring device includes an alert circuit for indicating when less than a predetermined number of doses remain to be dispensed.

45. The dosage monitoring system of claim 44 in which said alert circuit produces at least one of an audible and visual indication.

46. The dosage monitoring system of claim 24 in which said dosage monitoring circuit includes a reset circuit for clearing the present display of the circuit of the doses remaining when the inhalator canister being monitored is replaced.

47. A dispenser monitoring system for a dispenser actuatable along an actuation axis to dispense a quantity of material, comprising:
   a housing having a lower portion for mounting on a dispenser and an upper portion having a cavity; said actuation axis extending from said upper portion through such a dispenser which is affixed to the lower portion of said housing; said lower portion being tapered to be narrower at its lower end for accommodating a range of sizes of dispensers; and
   a dispenser monitoring circuit disposed in said cavity and including a switching device including an elastomeric membrane switch and at least one contact plate which is engaged by said membrane switch in response to actuation of such a dispenser, a counter circuit, responsive to said switching device, for registering that a quantity of material has been dispensed, and an electronic display device, responsive to said counter circuit, for indicating the status of the material in such a dispenser;
   said upper portion further including a rigid lower member which acts as a stop for said elastomeric membrane switch, said elastomeric membrane switch actuating said switching device via said at least one contact plate in response to actuation of such a dispenser.

48. The dispenser monitoring system of claim 47 in which said lower portion of said housing is flexible for securely gripping the dispenser.

49. The dispenser monitoring system of claim 48 in which said lower portion of said housing is flexible for securely gripping the inhalator canister.

50. An inhalator dosage monitoring system for a metered dose inhalator canister actuatable along an actuation axis to dispense a metered dose comprising:
   a housing having a lower portion for mounting on a metered dose inhalator canister, and an upper portion having a cavity; said actuation axis extending from said upper portion through such an inhalator canister which is affixed to the lower portion of said housing; said lower portion being tapered to be narrower at its lower end for accommodating a range of sizes of canisters; and
   a dosage monitoring circuit disposed in said cavity and including a switching device including an elastomeric membrane switch and at least one contact plate which is engaged by said membrane switch in response to actuation of such an inhalator canister, a counter circuit, responsive to said switching device, for registering that a dose has been dispensed, and an electronic display device, responsive to said counter circuit, for indicating the number of doses remaining in such an inhalator canister;
   said upper portion further including a rigid lower member which acts as a stop for said elastomeric membrane switch, said elastomeric membrane switch actuating said switching device via said at least one contact plate in response to actuation of such an inhalator canister.

51. A dispenser monitoring system for a dispenser actuatable along an actuation axis to dispense a quantity of material, comprising:
   a housing having a lower portion for mounting on a dispenser and an upper portion having a cavity; said actuation axis extending from said upper portion through such a dispenser which is affixed to the lower portion of said housing; and
   a dispenser monitoring circuit disposed in said cavity and including a switching device including an elastomeric membrane switch and at least one contact plate which is engaged by said membrane switch in response to actuation of such a dispenser, a counter circuit, responsive to said switching device, for registering that a quantity of material has been dispensed, an electronic display device, responsive to said counter circuit, for indicating the status of the material in such a dispenser; said display device includes a storage device for accumulating and storing for display the history of the number of dispenser actuations in a predetermined time period;
   said upper portion further including a rigid lower member which acts as a stop for said elastomeric membrane switch, said elastomeric membrane switch actuating said switching device via said at least one contact plate in response to actuation of such a dispenser.

52. An inhalator dosage monitoring system for a metered dose inhalator canister actuatable along an actuation axis to dispense a metered dose, comprising:
   a housing having a lower portion for mounting on a metered dose inhalator canister, and an upper portion having a cavity; said actuation axis extending from said upper portion through such an inhalator canister which is affixed to the lower portion of said housing; and
   a dosage monitoring circuit disposed in said cavity and including a switching device including an elastomeric membrane switch and at least one contact plate which is engaged by said membrane switch in response to actuation of such an inhalator canister, a counter circuit, responsive to said switching device, for registering that a dose has been dispensed, and an electronic display device, responsive to said counter circuit, for indicating the number of doses remaining in such an inhalator canister; said display device includes a storage device for accumulating and storing for display the history of the number of inhalator canister actuations in a predetermined time period;
   said upper portion further including a rigid lower member which acts as a stop for said elastomeric membrane switch, said elastomeric membrane switch actuating said switching device via said at least one contact plate in response to actuation of such an inhalator canister.

* * * * *